US008301246B2

(12) United States Patent
Park et al.

(10) Patent No.: US 8,301,246 B2
(45) Date of Patent: Oct. 30, 2012

(54) SYSTEM AND METHOD FOR IMPROVING CRT RESPONSE AND IDENTIFYING POTENTIAL NON-RESPONDERS TO CRT THERAPY

(75) Inventors: Euljoon Park, Valencia, CA (US); Xiaoyi Min, Thousand Oaks, CA (US)

(73) Assignee: Pacesetter, Inc., Sylmar, CA (US)

(*) Notice: Subject to any disclaimer, the term of this patent is extended or adjusted under 35 U.S.C. 154(b) by 278 days.

(21) Appl. No.: 11/759,756

(22) Filed: Jun. 7, 2007

(65) Prior Publication Data

US 2008/0306567 A1 Dec. 11, 2008

(51) Int. Cl.
*A61N 1/368* (2006.01)

(52) U.S. Cl. ........................................... 607/9

(58) Field of Classification Search .................. 600/373, 600/374, 393, 509, 516, 519; 607/7, 9, 11, 607/25, 27, 28, 116, 119, 122, 123
See application file for complete search history.

(56) References Cited

U.S. PATENT DOCUMENTS

| 4,712,555 | A | 12/1987 | Thornander et al. | |
|---|---|---|---|---|
| 4,788,980 | A | 12/1988 | Mann et al. | |
| 4,940,052 | A | 7/1990 | Mann et al. | |
| 4,944,298 | A | 7/1990 | Sholder | |
| 5,466,254 | A | 11/1995 | Helland | |
| 5,476,483 | A | 12/1995 | Bornzin et al. | |
| 6,314,323 | B1 | 11/2001 | Ekwall | |
| 6,978,184 | B1 * | 12/2005 | Marcus et al. | 607/120 |
| 7,310,554 | B2 * | 12/2007 | Kramer et al. | 607/9 |
| 7,899,520 | B2 * | 3/2011 | Lian et al. | 600/509 |
| 2002/0143264 | A1 | 10/2002 | Ding et al. | |
| 2002/0169484 | A1 | 11/2002 | Mathis et al. | |
| 2002/0177879 | A1 * | 11/2002 | Ding et al. | 607/9 |
| 2003/0014084 | A1 * | 1/2003 | VanHout | 607/9 |
| 2004/0106958 | A1 | 6/2004 | Mathis et al. | |
| 2004/0122479 | A1 | 6/2004 | Spinelli et al. | |
| 2004/0193223 | A1 | 9/2004 | Kramer et al. | |
| 2004/0215252 | A1 * | 10/2004 | Verbeek et al. | 607/9 |
| 2005/0090870 | A1 | 4/2005 | Hine et al. | |

FOREIGN PATENT DOCUMENTS

| WO | WO02/064205 | 8/2002 |
|---|---|---|
| WO | 02094372 A1 | 11/2002 |
| WO | WO2005/011475 | 2/2005 |
| WO | WO2005/039690 | 5/2005 |
| WO | 2007053064 A1 | 5/2007 |

OTHER PUBLICATIONS

Extended European Search Report, dated Sep. 16, 2008—EP App. No. 08251926.5.

* cited by examiner

*Primary Examiner* — Carl H Layno
*Assistant Examiner* — Frances Oropeza

(57) ABSTRACT

A method is disclosed that includes selecting an electrode configuration from a plurality of electrode configurations associated with electrodes of an implantable lead, sensing activity of the right ventricle and the left ventricle, determining an interval between sensed activity of the right ventricle and sensed activity of the left ventricle and determining whether the selected electrode configuration is suitable based at least in part on the interval. In one embodiment, an implantable device performs such a method to improve patient response to the CRT therapy, for example, by selecting a different electrode configuration if the current configuration is not suitable. Other exemplary methods, devices, systems, etc., are also disclosed.

11 Claims, 15 Drawing Sheets

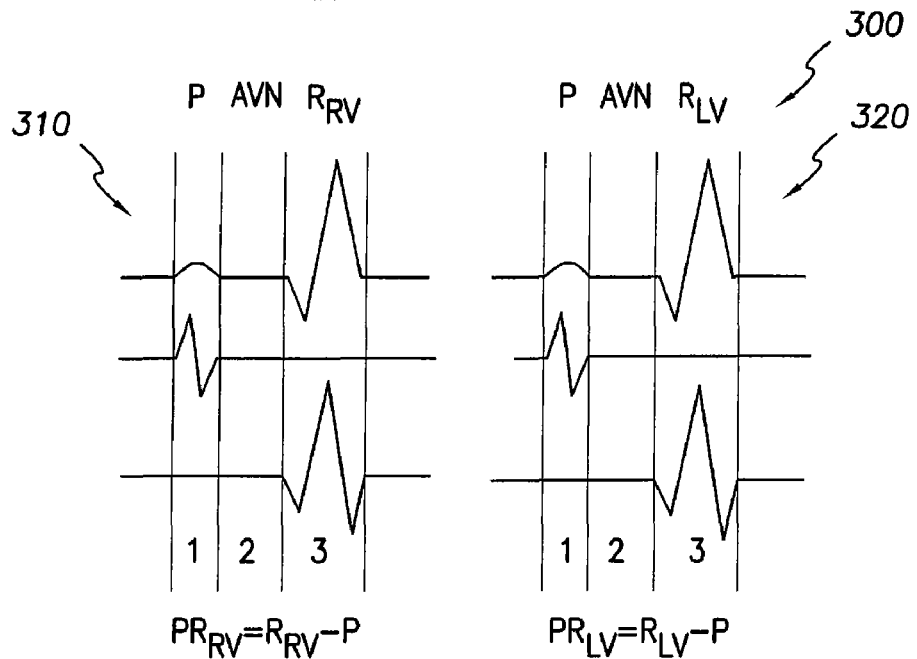
EXEMPLARY PR RHYTHMS
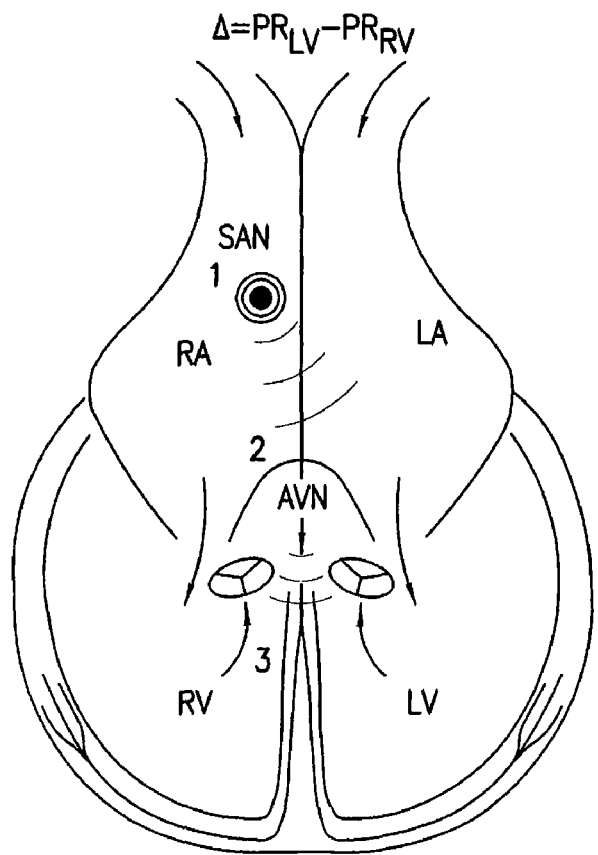
FIG. 3

EXEMPLARY AR RHYTHMS
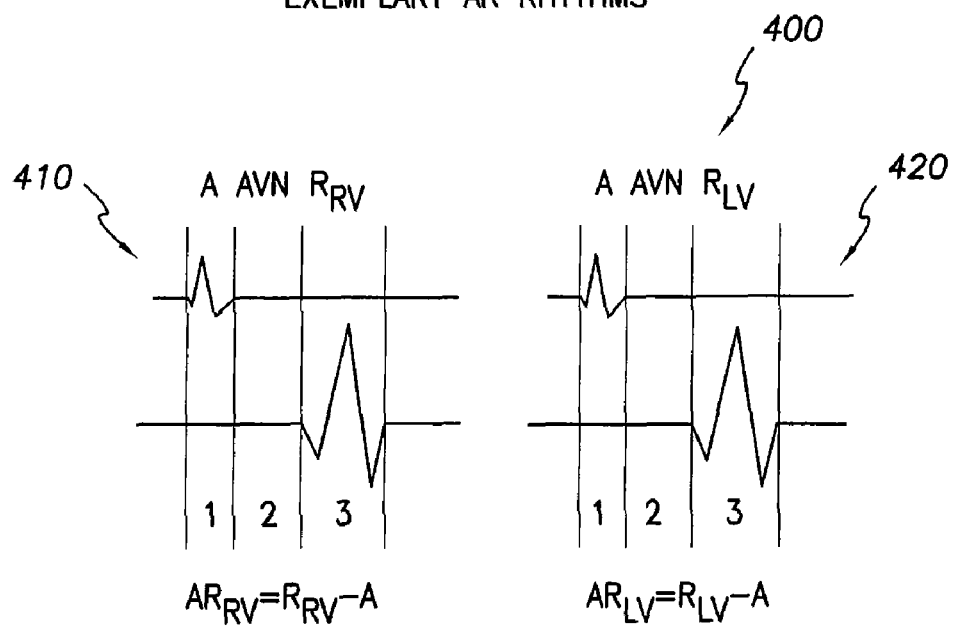
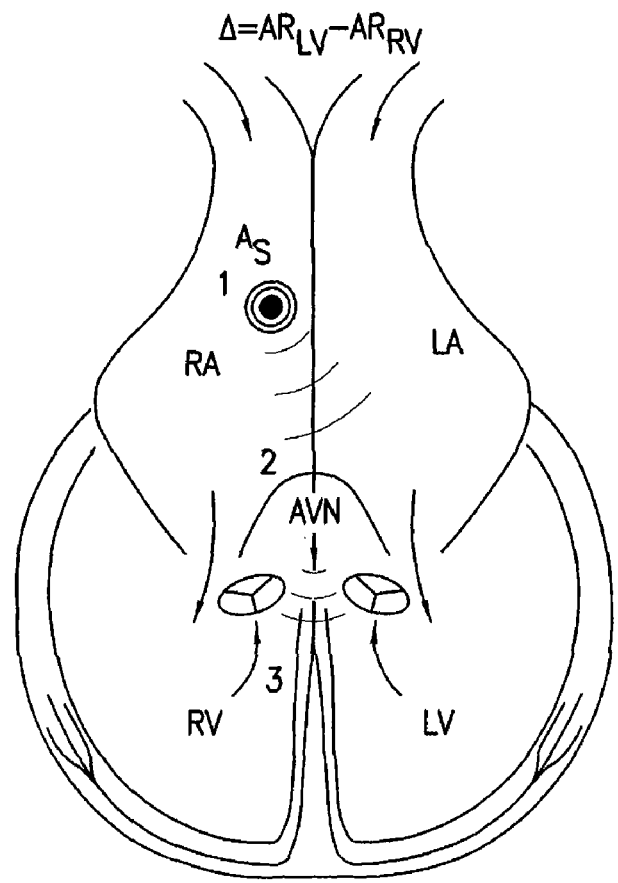
FIG. 4

INTERVENTRICULAR CONDUCTION
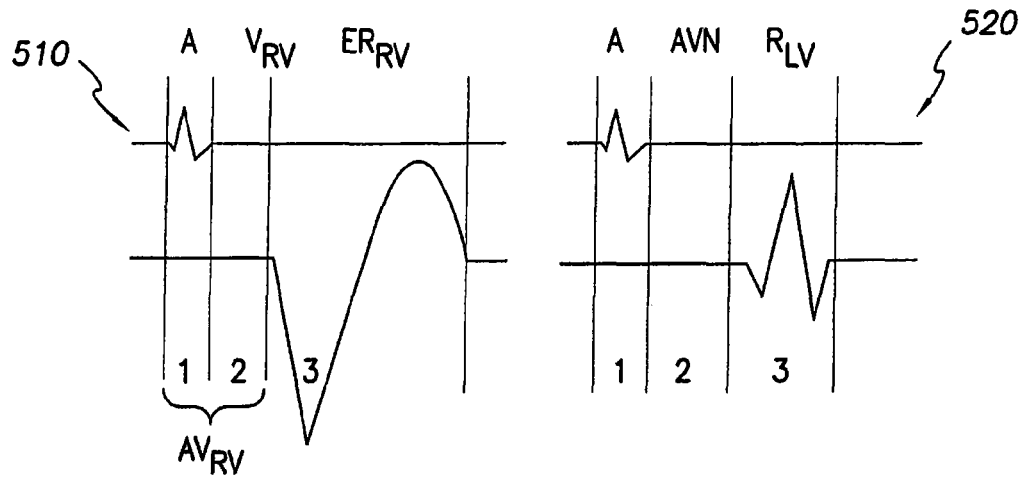
$PIVCD-RL = R_{LV} - V_{RV}$
$\Delta_{PIVCD} = (R_{RV} - V_{LV}) - (R_{LV} - V_{RV})$    $\Delta_{PIVCD} = PIVCD-LR - PIVCD-RL$
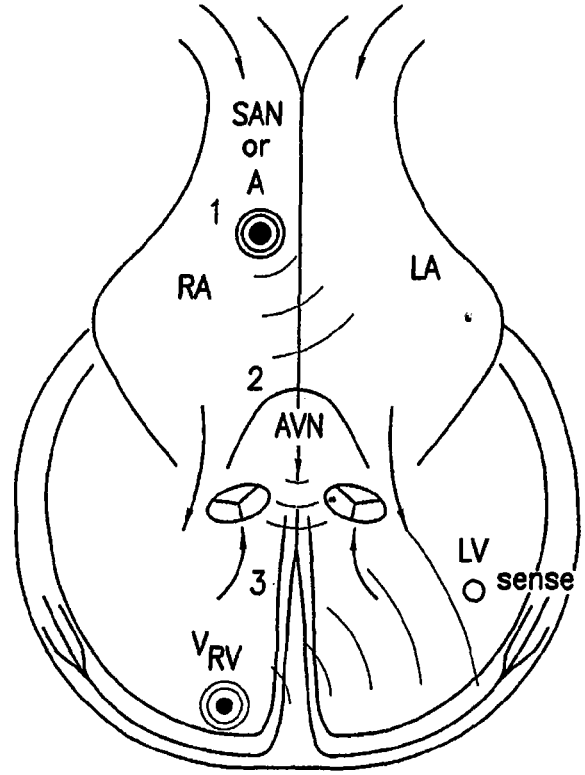
FIG. 5

INTERVENTRICULAR CONDUCTION
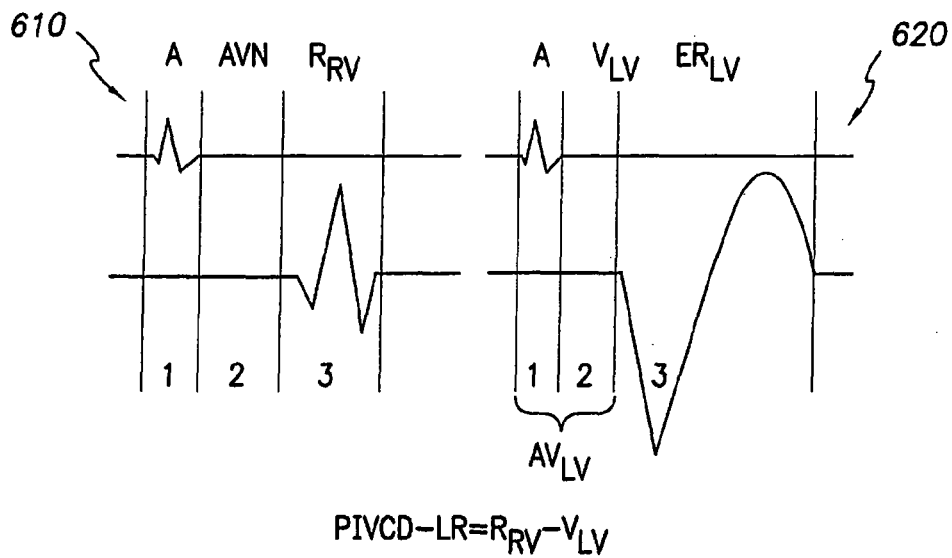
PIVCD-LR = $R_{RV} - V_{LV}$
$\Delta_{PIVCD} = (R_{RV} - V_{LV}) - (R_{LV} - V_{RV})$   $\Delta_{PIVCD}$ = PIVCD-LR − PIVCD-RL
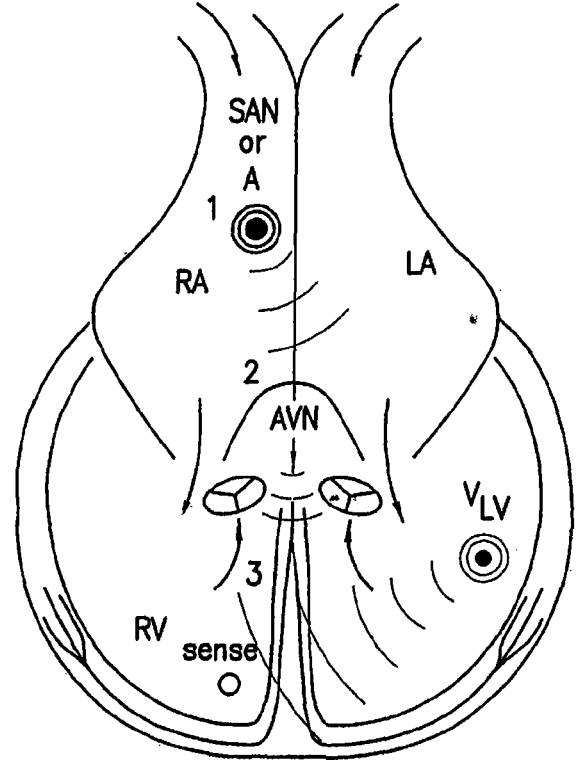
FIG. 6

INTRACARDIAC ELECTROGRAM (IEGM)
FOR PIVCD $AV_{RV}$      PROGRAMMED
$AR_{LV}$      MEASURED

PIVCD-RL = $AR_{LV} - AV_{RV}$

Implant

1402

|  | Δ | IVCD-RL | IVCD-LR |
|---|---|---|---|
| $LV_1$ | | | |
| $LV_2$ | | | |
| $LV_3$ | | | |
| $LV_4$ | | | |

Day N

1404

|  | Δ | IVCD-RL | IVCD-LR |
|---|---|---|---|
| $LV_1$ | | | |
| $LV_2$ | | | |
| $LV_3$ | | | |
| $LV_4$ | | | |

Day N + M

1406

|  | Δ | IVCD-RL | IVCD-LR |
|---|---|---|---|
| $LV_1$ | | | |
| $LV_2$ | | | |
| $LV_3$ | | | |
| $LV_4$ | | | |

SYSTEM AND METHOD FOR IMPROVING CRT RESPONSE AND IDENTIFYING POTENTIAL NON-RESPONDERS TO CRT THERAPY

CROSS-REFERENCE TO RELATED APPLICATIONS

This application is related to co-pending U.S. patent application Ser. No. 11/129,540, filed May 13, 2005, titled "System and Method for Improving CRT Response and Identifying Potential Non-Responders to CRT Therapy", which claims the benefit of U.S. Provisional Application Ser. No. 60/664,763, filed Mar. 23, 2005; and to co-pending U.S. patent application Ser. No. 10/703,070, filed Nov. 5, 2003. The foregoing three applications are incorporated by reference herein.

TECHNICAL FIELD

Exemplary methods and/or devices presented herein generally relate to cardiac pacing and/or stimulation therapy. Various exemplary methods and/or devices concern ventricular sensing and proper electrode selection and optionally lead placement based on the ventricular sensing.

BACKGROUND

Heart failure affects millions of people worldwide. Heart failure often manifests itself in relatively wide QRS signals, signifying a desynchronization between electrical activation of the right and left ventricles. Often, a left bundle branch block (LBBB) interrupts the normal conduction path to the left ventricle and results in the intrinsic conduction taking a relatively long time to reach the left ventricle, causing it to be activated well after the right ventricle. This dissynchrony results in a very inefficient contraction, resulting in very low cardiac output and patients who are unable to be very active. Over time, heart failure will progressively worsen and lead to death.

While some drug therapies may help some patients, electrical stimulation is more beneficial for those patients, assuming they meet certain criteria. Such stimulation is referred to as cardiac resynchronization therapy (CRT), which typically involves delivering electrical stimulation to the left ventricle prior to intrinsic conduction reaching the left ventricle, which results in a more synchronized contraction of the ventricles.

For patients who meet the current CRT implant criteria, a relatively large percentage (about 30%) of those patients do not respond to CRT therapy. What is needed is a system for increasing the likelihood that a patient will favorably respond to CRT therapy.

A new approach is proposed herein by using cardiac timing information to guide LV electrode selection and optionally lead placement for increasing the percentage of CRT responders.

SUMMARY

One embodiment disclosed herein is a method that uses IEGM data, specifically cardiac timing information, for properly selecting an electrode configuration and optionally positioning an LV lead. Such a method aims to increase the percentage of patients who have a positive response to CRT therapy. One embodiment disclosed herein is a method that includes selecting an electrode configuration from a plurality of electrode configurations associated with electrodes of an implantable lead, sensing activity of the right ventricle and the left ventricle, determining an interval between sensed activity of the right ventricle and sensed activity of the left ventricle and determining whether the selected electrode configuration is suitable based at least in part on the interval. In one embodiment, an implantable device performs such a method to improve patient response to the CRT therapy, for example, by selecting a different electrode configuration if the current configuration is not suitable. Other exemplary methods, devices, systems, etc., are also disclosed.

In one embodiment an interventricular conduction delay (IVCD) is determined by pacing the RV and sensing LV activation (IVCD-RL); alternatively, the system may pace the LV and sense RV activation (IVCD-LR). If IVCD is less than a threshold (<130 ms considering pacing latency), another LV electrode configuration is selected. Where possible (e.g., during implant) lead location may optionally be adjusted.

Alternatively, rather than IVCD, the intrinsic conduction delay ($\Delta$) may be determined by calculating either $|AR_{LV} - AR_{RV}|$ or $|R_{LV} - R_{RV}|$. If $\Delta$ is greater than a threshold (e.g., 80 ms) or within a pre-determined range (such as 80 ms<$\Delta$<300 ms), a proper LV electrode configuration is identified. If $\Delta$ is less than a threshold (e.g., 80 ms), IVCD is used for the tests. If IVCD is less than a threshold of 130 ms, an implantable device may select a different electrode configuration. In another alternative, a message may be displayed on a device programmer's user interface (UI) suggesting that a different LV electrode configuration and/or lead location be selected. Other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

FIG. 3 is an approximate anatomical diagram of a heart, a surface ECG and two IEGM waveforms that exhibit an intrinsic P wave and an R wave.

FIG. 4 is an approximate anatomical diagram of a heart and two IEGM waveforms that exhibit an A wave and an R wave.

FIG. 5 is an approximate anatomical diagram of a heart and two sets of IEGM waveforms wherein one set includes an evoked response in a right ventricle and the other set includes a response from a conducted event in a left ventricle.

FIG. 6 is an approximate anatomical diagram of a heart and two sets of IEGM waveforms wherein one set includes an evoked response in a left ventricle and the other set includes a response from a conducted event in a right ventricle.

FIG. 14 is a series of tables that include information related to electrode configuration and cardiac behavior or characteristics.

DETAILED DESCRIPTION

The following description includes the best mode presently contemplated for practicing the described implementations. This description is not to be taken in a limiting sense, but rather is made merely for the purpose of describing the general principles of the implementations. In the description that follows, like numerals or reference designators are used at times to reference like parts or elements throughout the description.

Overview

Exemplary methods, devices and/or systems pertain generally to proper electrode selection and/or placement for left ventricular pacing. For example, various exemplary methods include deciding whether a current location of a left-side electrode is suitable for CRT therapy and, if not, selecting a different electrode and optionally moving the electrode to a different location and repeating the process. In one embodiment, the timing delay between right ventricular activation and left ventricular activation is used to determine if the current location or selected electrode or electrode configuration is suitable.

The following description begins with a discussion of exemplary implantable devices and associated components followed by a discussion of heart rhythms and associated waveforms. Next, a discussion of cardiac performance follows, and the detailed description continues with a discussion of various exemplary methods, devices and/or systems.

Exemplary Stimulation Device

The techniques described below are intended to be implemented in connection with any stimulation device that is configured or configurable to stimulate nerves and/or stimulate and/or shock a patient's heart.

Figure 1:
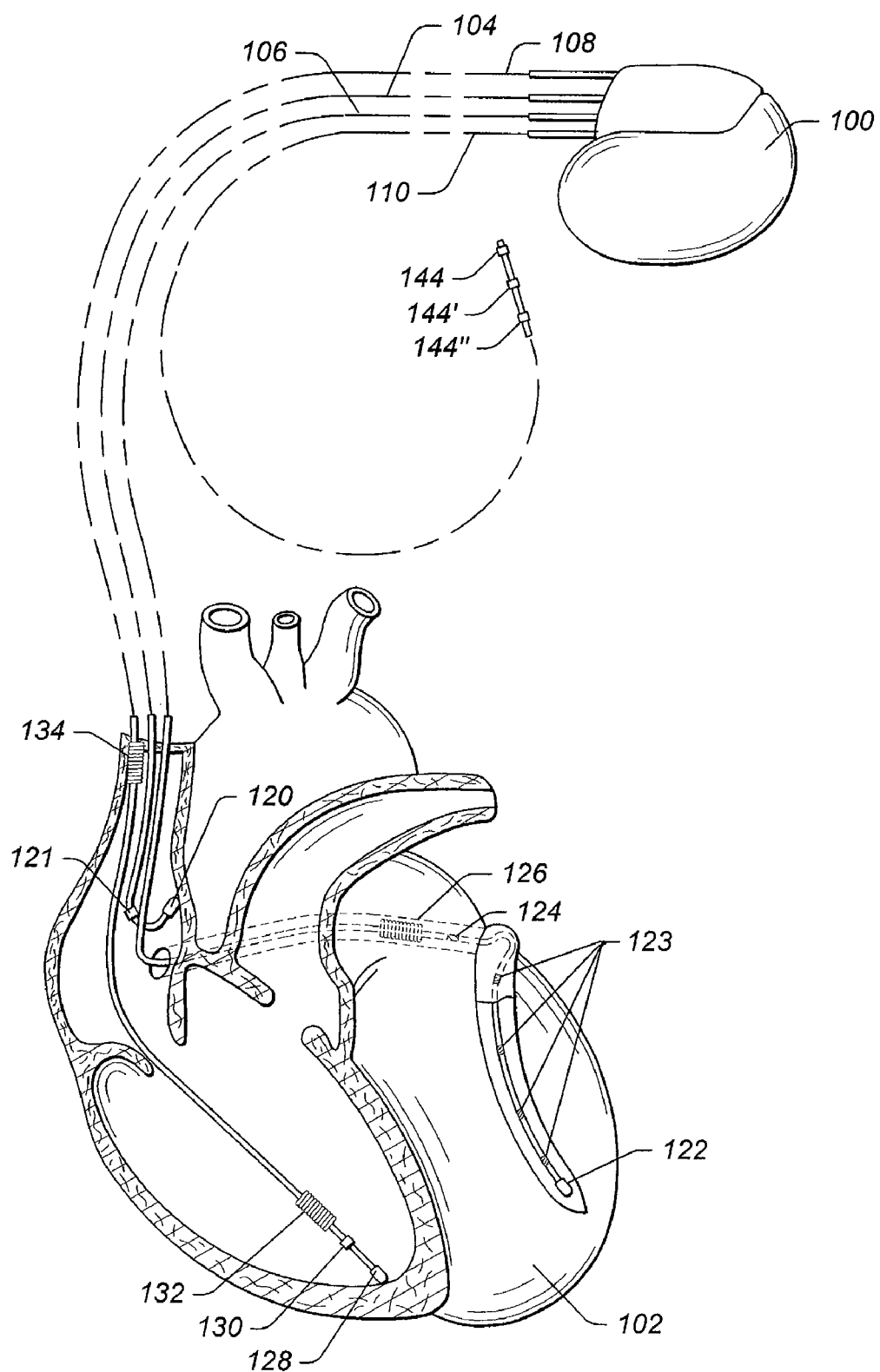
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 may optionally include a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein. As will be described in greater detail below, an illustrative method can test one or more placement locations of the coronary sinus lead 106 to determine a suitable placement for lead 106.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method selects one or more electrodes (e.g., from electrodes 123 of the lead 106) and determine characteristics associated with conduction and/or timing in the heart to aid in ventricular pacing therapy. As will be described in greater detail below, an illustrative method can test one or more electrodes of the coronary sinus lead 106 to determine a suitable electrode configuration for lead 106 (e.g., selection of one or more electrodes 123 of the lead 106).

An exemplary coronary sinus lead 106 can be designed to receive ventricular cardiac signals (and optionally atrial signals) and to deliver left ventricular pacing therapy using, for example, at least one of the electrodes 123 and/or the tip electrode 123. The lead 106 optionally allows for left atrial pacing therapy, for example, using at least the left atrial ring electrode 124. The lead 106 optionally allows for shocking therapy, for example, using at least the left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
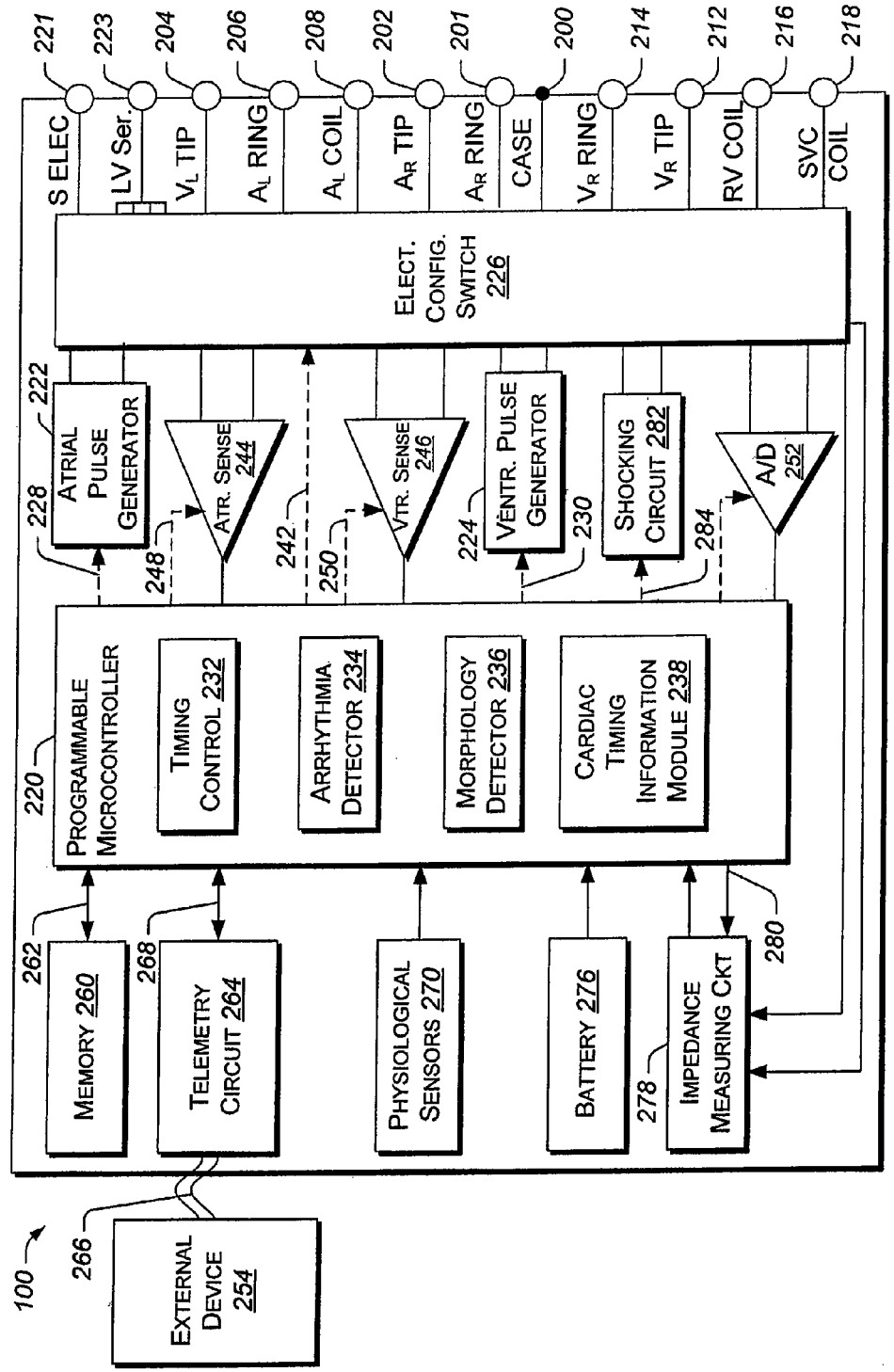
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardio-version, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121.

To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

Connection to suitable autonomic nerve stimulation electrodes is also possible via aforementioned terminals and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via the electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a cardiac timing information module 238 for determining one or more cardiac timing parameters. As described above, in one embodiment module 238 determines an intrinsic conduction delay between right ventricular activation and left ventricular activation. In other embodiments, module 238 determines an interval between stimulation of one ventricle and sensing of propagated electrical activity to the other ventricle. Module 238 may be implemented in hardware as part of the microcontroller 220, or as software/firmware instructions programmed into the device and executed on the microcontroller 220 during certain modes of operation. The function of module 238 is further described below in connection with FIGS. 10, 11, 13, 14 and 15.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Heart Rhythms

FIG. 3 shows an approximate anatomical diagram of a heart and two sets of PR waveforms 300. One set of waveforms 310 corresponds in part to right ventricular activity while another set of waveforms 320 corresponds in part to left ventricular activity. Action potentials propagating through a normal heart are labeled as follows: 1, associated with the sinoatrial node (SAN) and the atria; 2, associated with the atrio-ventricular node (AVN); and 3, associated with right and left bundle branches of the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

FIG. 3 also shows two surface electrocardiograms (ECG) of normal heart activity (e.g., polarization, depolarization, etc.) wherein atrial depolarization is represented as a "P wave" and ventricular depolarization is represented as an "R wave", or QRS complex. The right ECG shows a P wave followed by an AVN conduction delay (AVN) and a right ventricular R wave or QRS complex ($R_{RV}$). The left ECG shows a P wave followed by an AVN conduction delay (AVN) and a left ventricular R wave or QRS complex ($R_{LV}$). In this example, the right and left ventricular R waves ($R_{RV}$ and $R_{LV}$) are due to conduction through the atrio-ventricular node and not due to artificially paced events. The sets of plots 310, 320 include approximate atrial IEGM waveforms and approximate ventricular IEGM waveforms, for example, as sensed by an atrial sensing channel and one or more ventricular sensing channels.

Often detection of an R wave or QRS complex in an IEGM relies on signal amplitude or signal derivative with respect to time. Further, many detection methods are capable of assigning a time to a detected R wave or QRS complex or assigning a time span to a P wave to R wave or QRS complex interval, which are shown in FIG. 3 as $PR_{RV}$ for the right ventricle and $PR_{LV}$ for the left ventricle. If $PR_{RV}$ and $PR_{LV}$ are approximately equal, then the right ventricle and the left ventricle contract in a synchronous manner. For example, in a normal heart, the delay between contraction of the right ventricle and the left ventricle may be around 5 ms. However, if $PR_{RV}$ and $PR_{LV}$ differ substantially, e.g., $|\Delta|=|PR_{LV}-PR_{RV}|>5$ ms, then the right ventricle and left ventricle contract in an asynchronous manner, which may indicate some degree of cardiac dysfunction.) The embodiments described herein use the $\Delta$ value to determine whether the current lead positioning is adequate, or whether it needs to be changed.

The variable $\Delta$ represents an interventricular delay that is based on an atrio-ventricular delay for the left ventricle ($PR_{LV}$) and an atrio-ventricular delay for the right ventricle ($PR_{RV}$). The variable $|\Delta|$ is shown as the absolute value of the difference while herein and in the figures the variable $\Delta$ (e.g, $\Delta=PR_{LV}-PR_{RV}$) may be less than zero when $PR_{RV}$ exceeds $PR_{LV}$ or greater than zero when $PR_{LV}$ exceeds $PR_{RV}$. Described further below is a variable referred to as a paced interventricular conduction delay ($\Delta_{PIVCD}$), which relies on pacing in one ventricle and sensing in the other ventricle and optionally vice versa. A sensed interventricular conduction delay also exists, which corresponds to sensing an intrinsic event in one ventricle and subsequent sensing of consequences of this event in the other ventricle (e.g., depolarization). Both of these parameters are interventricular conduction delay (IVCD) parameters.

With respect to cardiac condition, a long interventricular delay may be indicative of a conduction block. For example, left bundle branch block (LBBB) may cause the left ventricle to contract more than approximately 50 ms after contraction of the right ventricle (e.g., $\Delta>0$). Whereas a right bundle branch block (RBBB) may be expected to cause the right ventricle to contract well after the left ventricle (e.g., $\Delta<0$). Of course, a patient may have RBBB and LBBB of similar extent such that interventricular delay does not indicate whether a block could be RBBB or LBBB. In such circumstances, atrio-ventricular delay may indicate block. For example, an atrio-ventricular delay of more than approximately 200 ms in a non-atrial paced heart may indicate some degree of block or conduction problem while an atrio-ventricular delay of more than approximately 250 ms in an atrial paced heart may indicate some degree of block or conduction problem.

FIG. 4 shows an approximate anatomical diagram of a heart and two sets of waveforms 400. One set of waveforms 410 corresponds in part to right ventricular activity while another set of waveforms 420 corresponds in part to left ventricular activity. Action potentials propagating through the heart are labeled as follows: 1, associated with a paced atrial stimulus and the atria; 2, associated with the atrio-ventricular node (AVN); and 3, associated with right and left bundle branches of the ventricles. In an atrial paced heart, cells depolarize near a pacing site (1) and thereby initiate an action potential (shown as dashed lines emanating from the pacing site). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

The two sets of waveforms 410, 420 show various IEGMs of heart activity (e.g., polarization, depolarization, etc.) wherein atrial depolarization is represented as an "A wave" and ventricular depolarization is represented as an "R wave", or QRS complex. Both sets 410, 420 show an A wave followed by an AVN conduction delay (AVN) and a right ventricular R wave or QRS complex ($R_{RV}$) for the set 410 and a left ventricular R wave or QRS complex ($R_{LV}$) for the set 420. Often detection of an R wave or QRS complex relies on signal amplitude or signal derivative with respect to time. Further, many detection methods are capable of assigning a time to a detected R wave or QRS complex or assigning a time span to an A wave to R wave or QRS complex interval, which are shown in FIG. 4 as $AR_{RV}$ for the right ventricle and $AR_{LV}$ for the left ventricle. If $AR_{RV}$ and $AR_{LV}$ are approximately equal, then the right ventricle and the left ventricle contract in an approximately synchronous manner. However, if $AR_{RV}$ and $AR_{LV}$ differ substantially, e.g., $|\Delta|=|AR_{LV}-AR_{RV}|>5$ ms, then the right ventricle and left ventricle contract in an asynchronous manner. Depending on patient or other factors, the time could be set at some time other than 5 ms. The variable $|\Delta|$ is shown as the absolute value of the difference while herein and in the figures the variable $\Delta$ (e.g, $\Delta=AR_{LV}-AR_{RV}$) may be less than zero when $AR_{RV}$ exceeds $AR_{LV}$ or greater than zero when $AR_{LV}$ exceeds $AR_{RV}$.

To facilitate measurement of $AR_{RV}$ or $AR_{LV}$, in instances where ventricular pacing occurs, the AV delay (e.g., $AV_{RV}$ and/or $AV_{LV}$) may be increased to a value greater than the expected $AR_{RV}$ or $AR_{LV}$. Of course, where possible, ventricular pacing is optionally disabled, set to a back-up mode, etc.

FIGS. 5 and 6 show plots, approximate anatomical diagrams and equations associated with yet another delay time, $\Delta_{PIVCD}$, referred to a paced interventricular conduction delay (PIVCD). FIG. 5 pertains to pacing in a right ventricle and sensing in a left ventricle wherein the time between pacing and sensing is referred to as a right to left PIVCD or PIVCD-RL, which equals $R_{LV}-V_{RV}$, wherein $V_{RV}$ is a pace time of a pacing stimulus in the right ventricle and $R_{LV}$ is a sense time of an evoked response wavefront in the left ventricle due to the paced stimulus in the right ventricle. Thus, PIVCD-RL is normally greater than zero. To ensure that the pacing stimulus in the right ventricle results in an evoked response, a capture routine or algorithm may be implemented. Thus, various exemplary methods, devices and/or systems include a capture algorithm (e.g., autocapture).

FIG. 5 shows a set of waveforms 510 that include an atrial event (e.g., A or P), an atrial to ventricular paced delay $AV_{RV}$, a ventricular pace time $V_{RV}$ and a sensed evoked response in the right ventricle $ER_{RV}$. Another set of waveforms 520 pertains primarily to the left ventricle and includes an atrial event (e.g., A or P), an AVN delay and a sensed evoked response in the left ventricle $R_{LV}$ which is a result of the stimulus $V_{RV}$ in the right ventricle. To ensure that the sensed evoked response in the left ventricle $R_{LV}$ is not due to conducted electrical activity from the atria, a sufficiently short ventricular paced delay $AV_{RV}$ is used. For example, a paced delay $AV_{RV}$ of approximately 30 ms to approximately 80 ms may suffice. $AV_{RV}$ may also be set sufficiently short to avoid fusion. While AV is referred to, PV may also apply where appropriate.

In general, bipolar sensing (or other multipolar/combipolar sensing) may increase signal to noise of the sensed activation in the left ventricle when compared to unipolar sensing that includes use of an in vivo, yet non-local electrode such as a pulse generator can. The latter technique is more often used in detection of evoked response or applications utilizing far-field signals. Further, bipolar sensing that includes two electrodes positioned in proximity to each other (e.g., less than approximately 4 cm), may increase signal to noise and sensitivity and better sense timing of an activation wave front proximate to the electrodes.

FIG. 6 pertains to pacing in a left ventricle and sensing in a right ventricle wherein the time between pacing and sensing is referred to as a left to right PIVCD or PIVCD-LR, which equals $R_{RV}-V_{LV}$, wherein $V_{LV}$ is a pace time of a pacing stimulus in the left ventricle and $R_{RV}$ is a sense time of a left ventricle, evoked response wavefront in the right ventricle due to the paced stimulus in the left ventricle. Thus, PIVCD-LR is normally greater than zero. To ensure that the pacing stimulus in the left ventricle results in an evoked response, a capture routine or algorithm may be implemented. Thus, various exemplary methods, devices and/or systems include a capture algorithm (e.g., autocapture).

FIG. 6 shows a set of waveforms 620 that includes an atrial event (e.g., A or P), an atrial to ventricular paced delay $AV_{LV}$, a ventricular pace time $V_{LV}$ and a sensed evoked response in the left ventricle $ER_{LV}$. Another set of waveforms 610 pertains primarily to the right ventricle and includes an atrial event (e.g., A or P), an AVN delay and a sensed evoked response in the right ventricle $R_{RV}$ which is a result of the stimulus $V_{LV}$ in the left ventricle. To ensure that the sensed evoked response in the right ventricle $R_{RV}$ is not due to conducted electrical activity from the atria, a sufficiently short ventricular paced delay $AV_{LV}$ is used. For example, a paced delay $AV_{LV}$ of approximately 30 ms to approximately 80 ms may suffice. $AV_{LV}$ may also be set sufficiently short to avoid fusion. While AV is referred to, PV may also apply where appropriate.

In general, bipolar sensing (or other multipolar/combipolar sensing) may increase signal to noise of the sensed activation response in the left ventricle when compared to unipolar sensing that includes use of an in vivo, yet non-local electrode such as a pulse generator can. The latter technique is often more used in detection of evoked response or the applications utilizing far-field signals. Further, bipolar sensing that includes two electrodes positioned in proximity to each other (e.g., less than approximately 4 cm), may increase signal to noise and sensitivity and better localize an activation wavefront.

Various exemplary methods described herein are optionally implemented using an implantable device having a single sensing channel for one or more electrodes positioned in or on the right ventricle and for one or more electrodes positioned in or on the left ventricle. In such devices, switching is optionally used to switch between sensing of the right ventricle and the left ventricle. Alternatively, both ventricles are sensed at the same time wherein an algorithm or other detection method is used to distinguish at least some information associated with the right ventricle from at least some information associated with the left ventricle.

Figure 7:
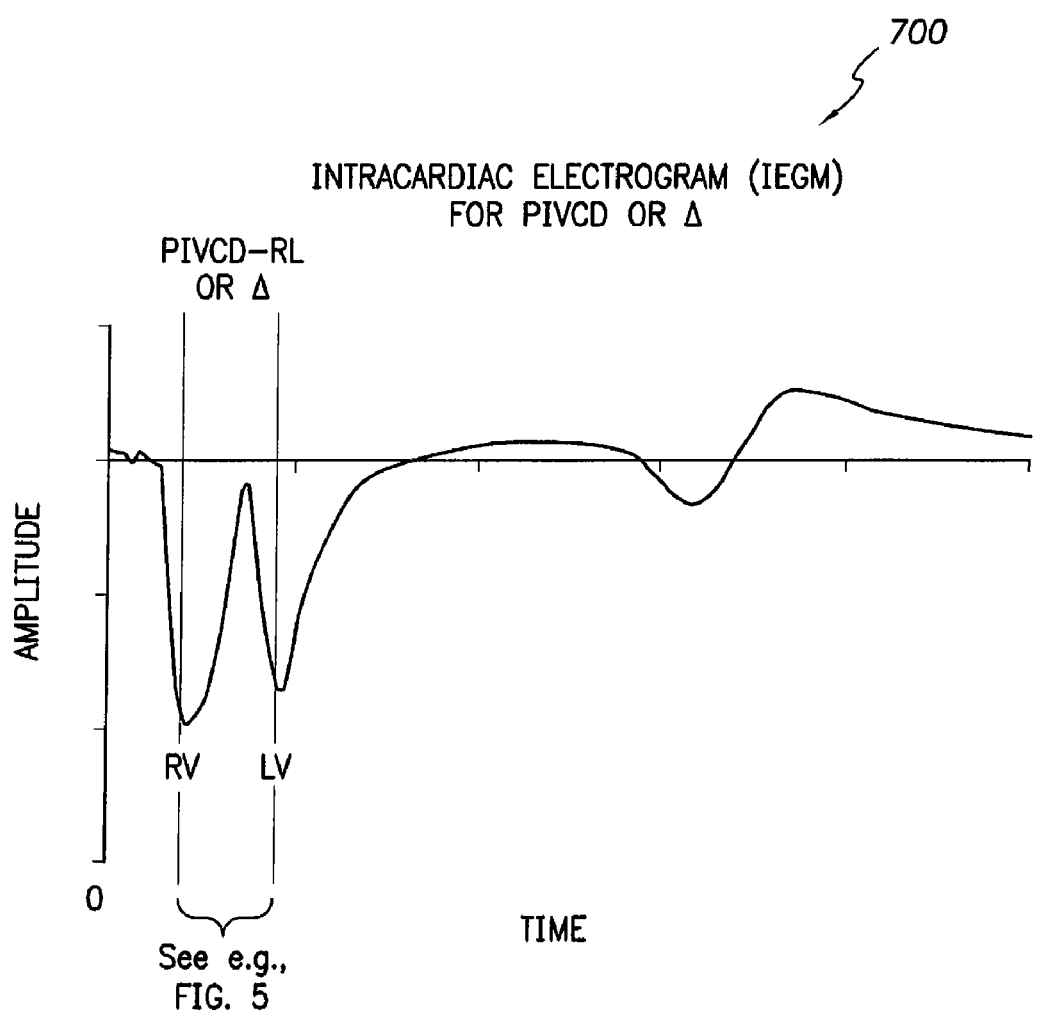
FIG. 7 is an exemplary IEGM plot acquired in a study using a unipolar sensing arrangement for a right ventricular tip electrode and a left ventricular tip electrode having a common electrode.

FIG. 7 shows an exemplary IEGM plot 700 acquired in a study using a unipolar sensing arrangement for a right ventricular tip electrode and a left ventricular tip electrode having a common electrode (e.g., can, device sensing circuit, etc.). In this unipolar arrangement, an electrical connection exists between right and left ventricular sensing circuits. In particular, depolarization due to atrio-ventricular intrinsic conduction was sensed at the right ventricle and then sensed at the left ventricle as the activation propagated to the left ventricle, and is identified by the two discernible peaks shown in FIG. 7 and corresponding to right ventricular activation and left ventricular activation, respectively. In this example, the peak-to-peak time delay typically approximates Δ and may be used to determine whether the lead positions are suitable. However, it may approximate PIVCD-RL in the case of FIGS. 5 and 6. If RV is paced at a short AV delay (such that no intrinsic conduction will have yet arrived at the ventricles), the time delay from pacing RV to the peak of the conduction to the left ventricle approximates PIVCD-RL. In an alternative example, not shown in FIG. 7, a pacing stimulus may be delivered to the right ventricle at a time of approximately 0 ms. This pacing stimulus will result in capture of the right ventricle and the IEGM will show a corresponding right ventricular evoked response. In this example, the left ventricle is not paced or initially captured by the pace to the right ventricle but after a short delay, the left ventricle will depolarize due to conduction of the paced event from the right ventricle. Hence, the delay between the right ventricular peak (RV) and the left ventricular peak (LV) approximates a paced interventricular conduction delay from right ventricle to left ventricle (see, e.g., PIVCD-RL of FIG. 5). Thus, the plot 700 helps to demonstrate a particular exemplary manner in which an implantable device that uses a single sensing amplifier for right and left ventricular sensing channels can determine paced interventricular conduction delay.

Further, some implantable devices having sensing and pacing capabilities can deliver a stimulus to one ventricle and then switch to sensing of both ventricles. For example, in the plot 700, the RV stimulus may have been delivered in an open configuration (e.g., RV and LV leads/electrodes not "connected") and, thereafter, leads/electrodes "shorted" to allow for sensing from both ventricles. Of course, where appropriate, pacing in one ventricle and sensing in the other ventricle may occur according to various arrangements.

Figure 8:
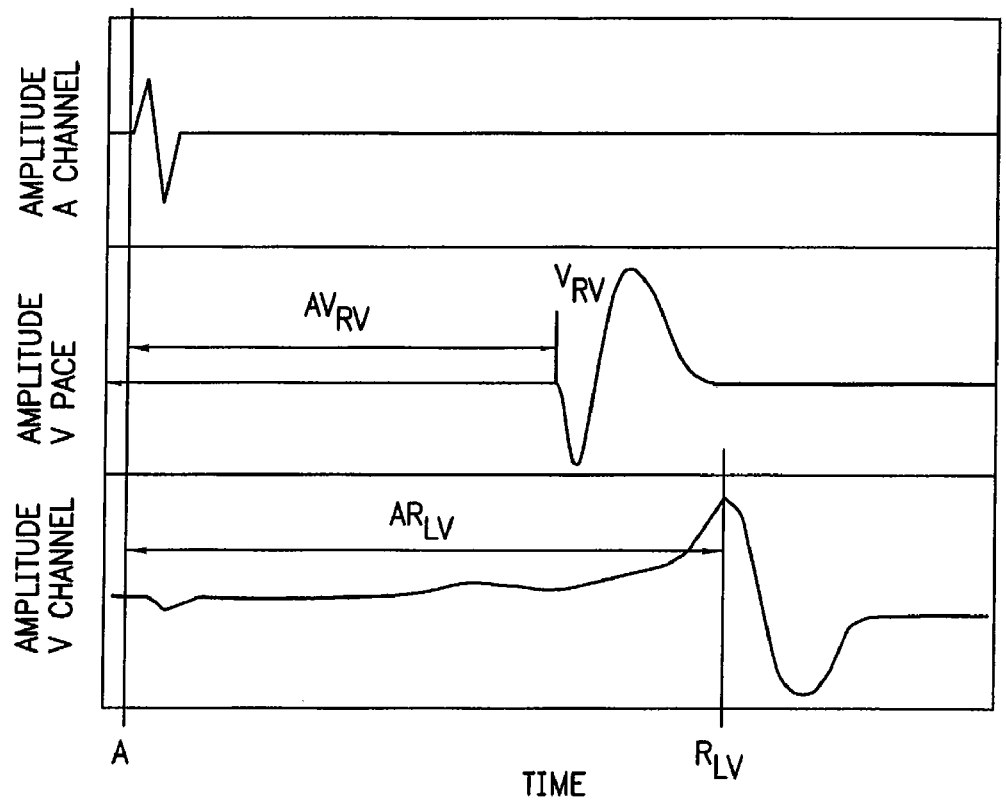
FIG. 8 is an exemplary atrial and ventricular IEGM plot acquired in a study using an implantable device optionally including a switchable channel for RV and LV sensing and/or pacing.

FIG. 8 shows an exemplary IEGM plot 800 wherein the ventricular IEGM was acquired using an implantable device including a switchable channel for RV and LV sensing. Such a device may allow for measurement of $AR_{RV}/PR_{RV}$ and $AR_{LV}/PR_{LV}$ by switching between RV sensing to LV sensing. Accordingly, Δ may be ascertained. Such a device may also allow for pacing in the right ventricle and/or left ventricle. Further, such a device may ascertain PIVCD-RL and/or PIVCD-LR. For example, if an $AV_{RV}$ or $PV_{RV}$ delay is set short enough to avoid fusion, then $AR_{LV}$ or $PR_{LV}$ may be determined on the basis of LV sensing wherein the LV sensing sense electrical activity in the left ventricle (e.g., $R_{LV}$) stemming from the right ventricular stimulus (e.g., $V_{RV}$). In this example, PIVCD-RL may equal $AR_{LV}-AV_{RV}$ or $PR_{LV}-PV_{RV}$.

Other implantable devices may include RV and LV sensing channels that can operate at the same time. Such devices may allow for measurement of $AR_{RV}/PR_{RV}$ and $AR_{LV}/PR_{LV}$ on a beat-by-beat basis. For example, for a single beat, an atrial to right ventricular delay and an atrial to left ventricular delay may be ascertained. Such an exemplary method can reduce measurement error by determining such variable for a single beat as compared to determining one variable for one beat and another variable for a different beat. Detection of an event may be based on sensitivity programmed in devices or a criterion such as an amplitude value greater than approximately 40% of an expected QRS amplitude value.

Various exemplary methods, devices and/or systems may help to avoid cross ventricular sensing. For example, if an interventricular delay is less than interventricular conduction (e.g., PIVCD-RL and PIVCD-LR), the incidence of sensing paced ventricular events in an alert interval is reduced. Further, this incidence may be further reduced through use of an automatic capture algorithm.

Figure 9B:
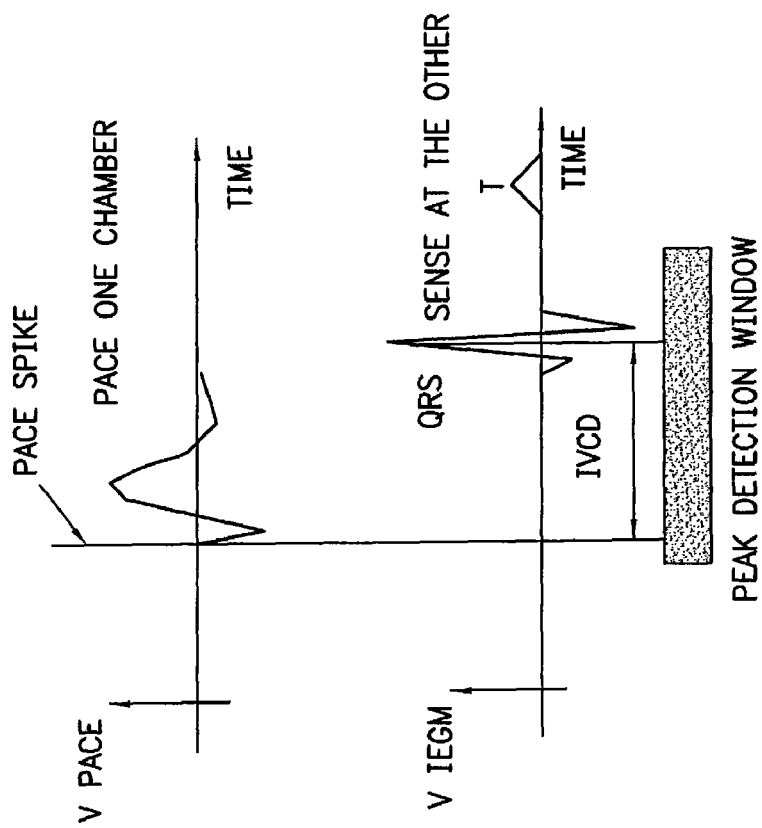
FIGS. 9A and 9B depict ventricular activity as sensed by independent sense channels and illustrate an embodiment in which the atrial activity is not required.
Figure 9A:
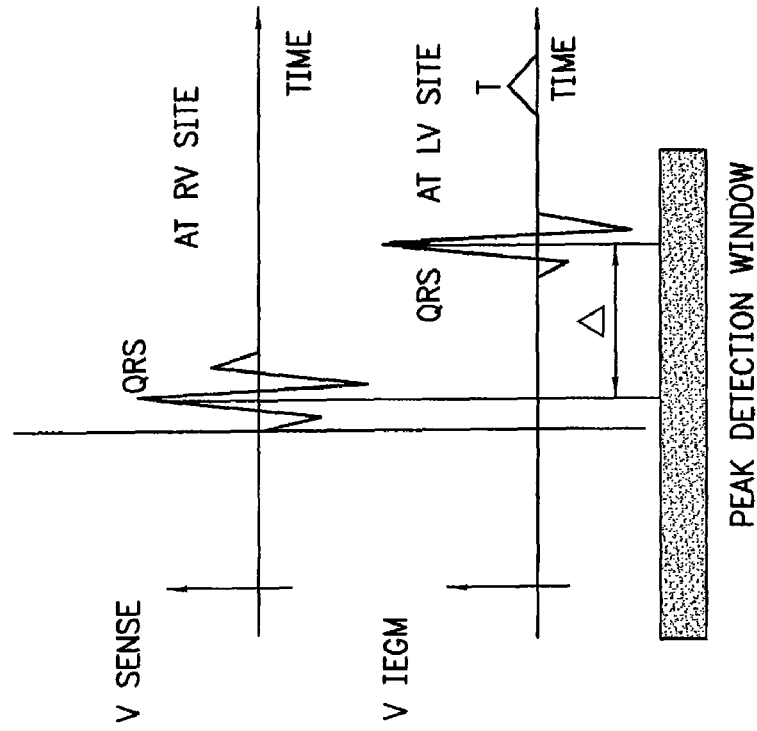

FIGS. 9A and 9B show exemplary IEGM plots 900 of ventricular activity as sensed by a pair of sensing channels, V SENSE and V IEGM. This ventricular activity may be used in one embodiment that does not rely on atrial activity to determine IVCD or Δ; rather, by simply monitoring the right ventricular and left ventricular activity, an IVCD or Δ value can be determined. As shown in FIG. 9A, the Δ value can be determined by monitoring a first channel (the "V SENSE" channel) for right ventricular activity and a second channel (the "V IEGM" channel) for left ventricular activity. While many different ways of detecting activity can be employed, in this embodiment the peaks are used to detect activity, and the peak-to-peak interval is used to determine the Δ value. In addition, while the RV is shown as being the first ventricle to intrinsically activate, it will be understood that in some patients the LV may activate prior to the RV.

As shown in FIG. 9B, a ventricular pace spike in one chamber (e.g., the right ventricle) initiates the IVCD interval, and detection of the peak of the QRS on the V IEGM channel signifies the end of the IVCD interval. Alternatively, capture verification may be performed in the first chamber (e.g., to detect the peak of the evoked response), and the IVCD interval can be initiated at that point rather than upon delivery of the pacing pulse.

Figure 10:
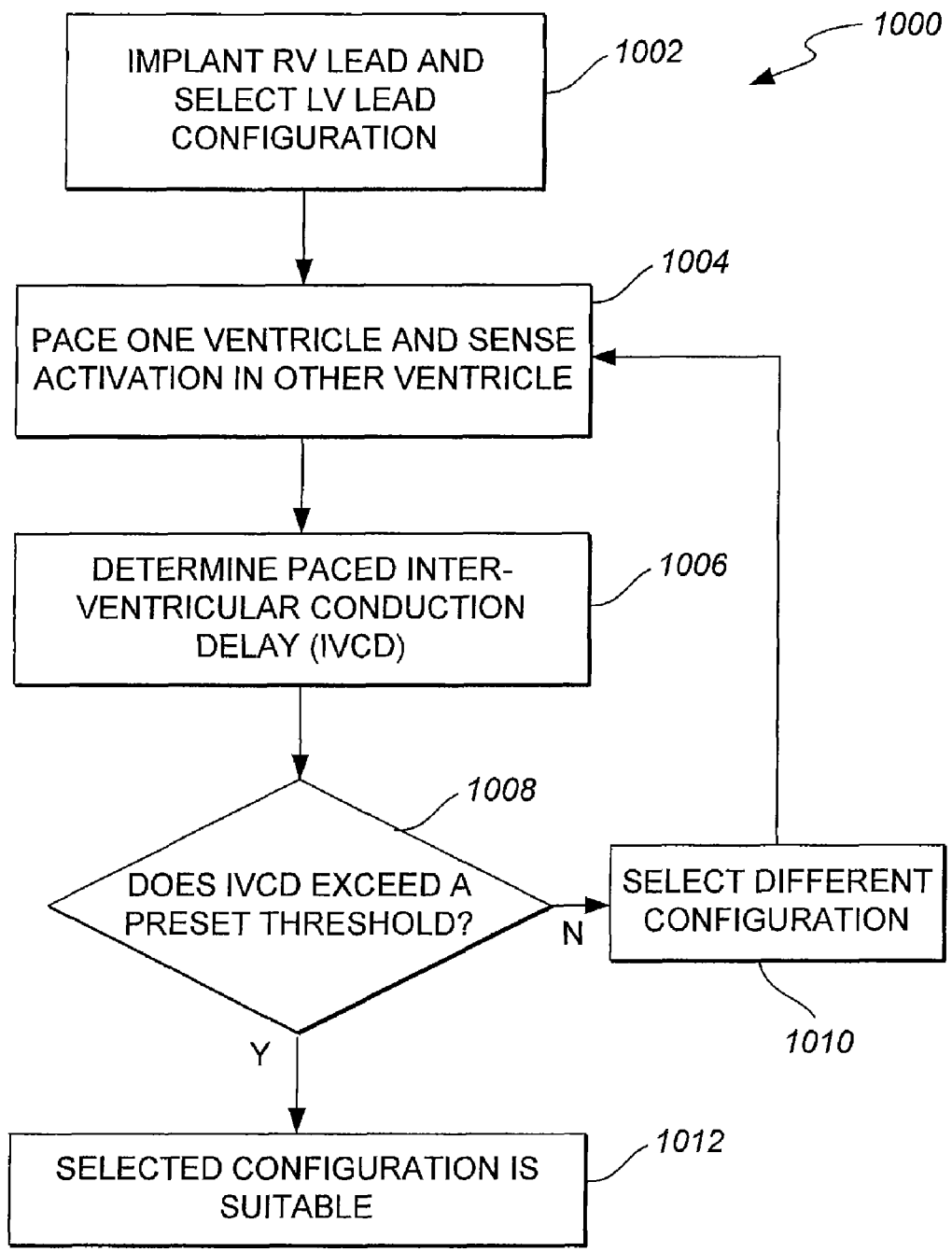
FIG. 10 is a flow chart of another exemplary method for determining whether electrode configuration is suitable for CRT therapy.

Referring now to FIG. 10, an illustrative method 1000 is shown for determining the suitability of a particular electrode configuration. For example, a LV lead that includes a series of electrodes, such as the lead 106 and electrodes 123, may be used in performing the method 1000. At step 1002, the clinician implants an RV lead capable of delivering stimulation energy to the right ventricle and sensing cardiac activity. In addition, at step 1002, the clinician locates an LV lead at a site for stimulating the left ventricle (e.g., through the coronary sinus, epicardially, pericardially, etc.) and selects an initial electrode configuration that includes one or more electrodes of the lead for use in delivery of stimulation energy. The particular electrode configuration may also be used for sensing cardiac activity, for example, activity indicative of myocardial conduction times or delays.

At step 1004, stimulation energy is delivered to one ventricle in a manner that is also likely to cause depolarization of the other ventricle. Accordingly, sensing can acquire information to determine an interventricular conduction time from IVCD-RL and/or IVCD-LR. For example, the clinician may cause a stimulation pulse to be delivered to the left ventricle via the selected LV electrode configuration to thereby cause the left ventricle to depolarize. The RV lead is then used to acquire information as the depolarization waveform conducts from the left to the right ventricle. This particular embodiment is suitable for use with patients who suffer from LBBB or other left-sided conduction problems. For patients suffering from RBBB or other right-sided conduction problems, the right ventricle can be paced and the corresponding activity sensed in the left ventricle. While various LV leads are shown and discussed as including a series of electrodes, such techniques may be applied to RV leads, as appropriate.

At step 1006, the interval between delivery of the stimulation pulse in the one ventricle and the sensed activity in the other ventricle is determined to be the IVCD. At decision block 1008, a determination is made whether the IVCD exceeds a threshold value. In one embodiment, the threshold value is on the order of 80 milliseconds or more, preferably about 130 milliseconds. Thus, if the IVCD does not exceed the threshold, operation proceeds to step 1010 and the system recommends that the clinician select a different electrode configuration. In addition, or alternatively, the LV lead may be moved to a different location. Once a different electrode configuration has been selected (and possibly a new lead location), the method 1000 returns to step 1004 and where steps 1004, 1006 and 1008 are repeated, if appropriate. For example, where a LV lead includes a series of four electrodes, given a particular LV lead placement, if no electrode configuration satisfies the condition of block 1008, then the lead placement may be changed (i.e., to a new lead location). Of course, if no placement or electrode configuration satisfies the desired criterion (or criteria), then a clinician may select a lead placement and/or electrode configuration based at least in part on the acquired information.

If, on the other hand, the IVCD value does exceed the threshold value, operation proceeds to step 1012 and the clinician is advised that the selected electrode configuration for the tested lead placement is suitable for CRT therapy. The clinician may then continue to implant the medical system and program the implantable medical device, including programming interval values for delivering CRT therapy.

As described above, for patients suffering from RBBB or other right-side conduction problems, the LV lead may be implanted in a desired location, and the RV lead may be advanced to a site for testing, with the above-described method being carried out; if the IVCD value does not exceed a threshold value, the electrode configuration of the RV lead may be altered and/or the RV lead moved until a suitable IVCD value is identified.

Figure 11:
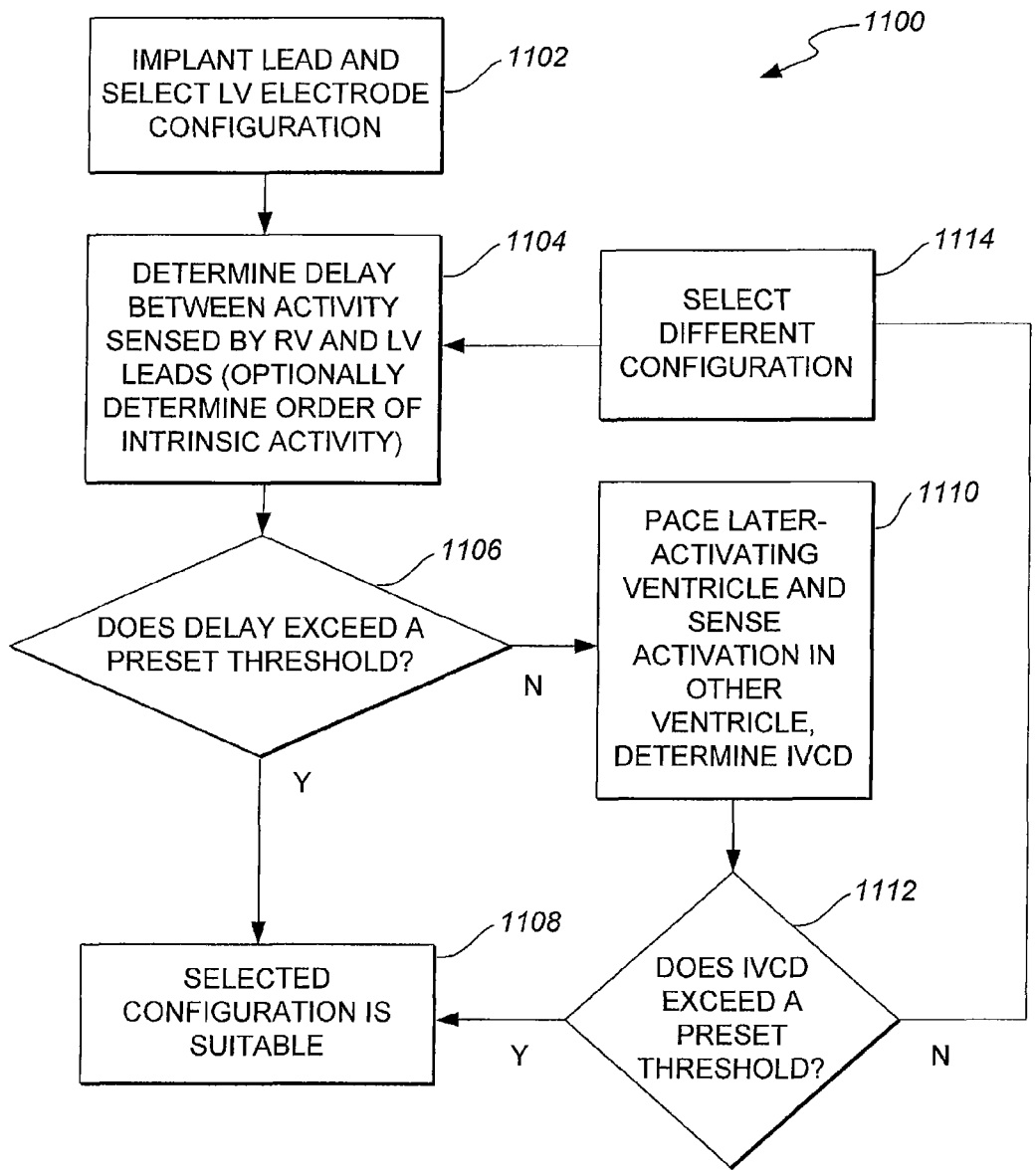
FIG. 11 is a flow chart of another exemplary method for determining whether electrode configuration is suitable for CRT therapy

FIG. 11 shows a flow chart of a method 1100 for determining proper electrode selection according to another illustrative embodiment. According to the method 1100, one or more leads bearing electrodes are placed for communication with the RV and LV, respectively, at step 1102. In one embodiment, the clinician implants a RV lead in the right ventricle and advances a LV lead through the coronary sinus and into one of the coronary veins that overlie the left ventricle.

The method 1100 may proceed via a surgical process where the selection of electrode configuration and optionally lead repositioning occur or the method 1100 may proceed via a post-operative electrode configuration selection process. In the former process, a clinician connects the lead(s) bearing a series of electrodes to a suitable test device, for example, either the implantable medical device, an external pacing system analyzer, the programmer through a suitable adapter, or any other suitable device for processing the sensed IEGM data. In the latter process, the lead(s) bearing a series of electrodes are connected to an implantable device (e.g., the device 100 of FIGS. 1 and 2) where a clinician may direct one or more steps and/or where the device includes control logic capable of executing one or more steps, either automatically or via external direction (e.g., a control signal delivered telemetrically to the implanted device).

At step 1104, the intrinsic conduction delay Δ is determined based on the interval between activity detected in the RV and activity detected in the LV. For example, a test device (whether implantable and/or external) may passively monitor the cardiac activity and detect intrinsic activity of the RV and LV, where the delay $\Delta$ is computed as the interval between RV and LV activation. In another embodiment, a test device determines an $AR_{RV}$ time and an $AR_{LV}$ time (or a $PR_{RV}$ time and a $PR_{LV}$ time) and computes $\Delta$ as the difference between the two values ($AR_{RV}$-$AR_{LV}$ or $PR_{RV}$-$PR_{LV}$).

At step 1104, the system optionally determines the order in which intrinsic activity was detected in the right and left ventricles (i.e., which ventricle experiences intrinsic activity first and which one experiences intrinsic activity last) if it has not already been determined a priori. For a patient known to have LBBB or RBBB, for example, this determination will not be necessary as the clinician already knows which ventricle is too slow in activating. This information can be used in step 1110 to determine which ventricle to pace and which ventricle to sense for determining an IVCD value, as described in greater detail below.

At decision block 1106, a determination is made whether $\Delta$ exceeds a threshold value, for example 80 ms. If so, operation proceeds to step 1108 and the selected electrode configuration (and lead placement) is deemed suitable for CRT therapy. Where an external device is used to facilitate selection or placement, an optional message may be displayed on a user interface to indicate as such to the clinician.

In one embodiment, the delay value preferably exceeds a threshold value, which may be greater than 30 milliseconds and preferably about 80 milliseconds.

In another embodiment, the delay value is preferably within a range of values, for example between about 20 milliseconds and about 200 milliseconds, more preferably between about 30 and about 160 milliseconds. If the delay value does not exceed the lower limit of the range, operation proceeds to step 1110 as described below. In addition, if the delay value exceeds the upper limit of the range, then a computing system (whether an implantable device or external device) may recommend selection of a different configuration and/or movement of a lead or leads.

On the other hand, if $\Delta$ does not exceed the threshold value, the method 1100 proceeds to step 1110. At step 1110, the system determines the IVCD value by 1) delivering a stimulation pulse (preferably at a very short AV delay) to the ventricle that experienced intrinsic activity last, 2) sensing corresponding activity in the other ventricle (i.e., the ventricle that intrinsically activated first), and 3) determining an interval between either A) the delivery of the pulse in the first ventricle and detection of activity in the other ventricle, or B) verification of capture in the first ventricle and detection of activity in the other ventricle.

In one embodiment, where intrinsic activity is detected last in the LV, the pacing pulse is delivered to the LV in a subsequent cycle and at a short AV delay, and the conducted activity is sensed in the RV (IVCD-LV). Alternatively, where intrinsic activity is detected last in the RV, the RV is paced at a short AV delay and the conducted activity is sensed in the LV (IVCD-RV).

The IVCD is then compared with a threshold at query block 1112. The threshold may differ depending upon which interval calculation method was used. For example, the threshold can be on the order of about 130 milliseconds, when the interval is between delivery of the pulse and detection of activity in the other ventricle. On the other hand, the threshold can be on the order of about 80, when the interval is between verification of capture in the first ventricle and detection of activity in the other ventricle.

If the IVCD exceeds the threshold, then operation proceeds to step 1108 and the placement is considered suitable for CRT therapy. If not, the method 1100 proceeds to step 1114 where an implantable device may automatically select a different electrode configuration, issue an alert and/or take other appropriate action. Where a clinician guides the method, then a computing device may issue an alert such that a different electrode configuration is considered and tested and/or a new lead(s) position is considered and tested.

In one embodiment, an interventional process, the clinician may move the LV lead, either to a new location within the same cardiac vein or withdraw it from the cardiac vein and then advance it through a different cardiac vein. Once the clinician has moved the lead to the next proposed location, operation returns to step 1104 and the process is repeated. If no suitable location, for a variety of electrode configurations, is found after multiple sites and configurations are tested, the clinician may either withdraw the LV lead and implant an epicardial lead, or choose one of the tested sites and program the implantable medical device with the knowledge that the site may not be optimal for CRT therapy. Where an epicardial lead includes a series of electrodes, various exemplary methods may be used to select an appropriate electrode configuration of the epicardial lead using a criterion or criteria as already mentioned.

It will be understood by those skilled in the art that the sensing described herein can be done in a unipolar configuration, i.e., between an electrode implanted in the heart and the device housing, or in a bipolar configuration, i.e., between a pair of electrodes implanted in the heart. Bipolar sensing can be done with a truly bipolar lead (having a tip electrode and closely spaced ring electrode), or an integrated bipolar lead (having a tip electrode and a defibrillation coil used to sense electrical activity). Multipolar configurations are also possible given a lead bearing a plurality of electrodes (e.g., the lead 106 and electrodes 123). A multipolar configuration may include use of a can electrode and/or an electrode on a different lead.

In an alternate embodiment, one or both of the RV and LV leads can be epicardial leads connected to the outside of the heart over the RV and LV, respectively, or one or both of the RV and LV leads can be replaced by satellite electrodes that telemeter information to a remote device.

As mentioned above, in some implant procedures the LV lead will be implanted prior to the RV lead, and it will be desirable to test the location of the LV lead and electrode configuration of the LV lead, and possibly reposition and/or select a different electrode configuration, as necessary, prior to implanting the RV lead. In this instance, a surface ECG signal may be used in place of the RV lead. In particular, a vector may be chosen that replicates the IEGM signal detected by an RV lead at the RV apex, for example lead V2, lead V1, lead V3, and/or lead II.

Figure 12:
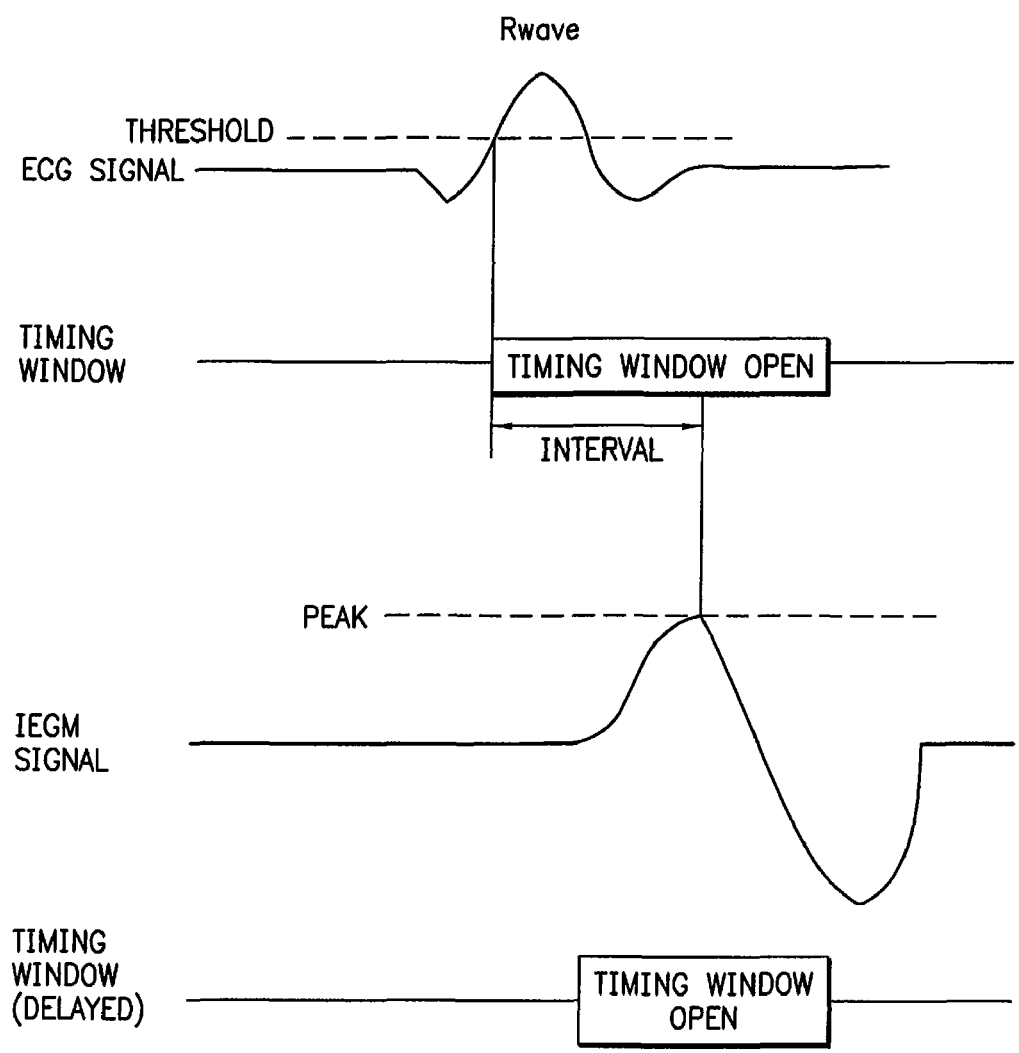
FIG. 12 is an exemplary plot of ECG and IEGM data to be used in accordance with another exemplary method.
Figure 13:
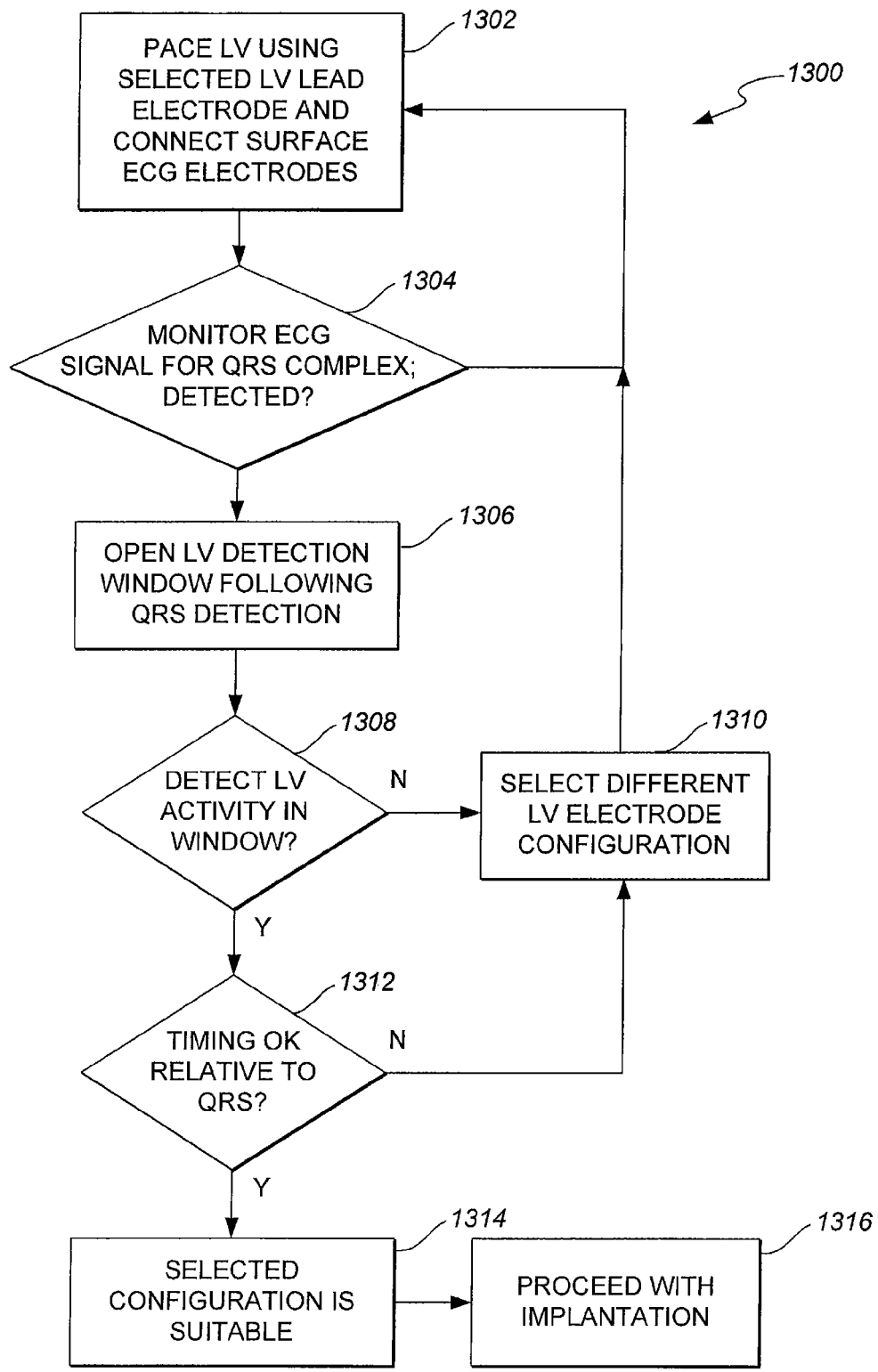
FIG. 13 is a flow chart of a method that uses the data from FIG. 12.

Referring to FIGS. 12 and 13, another embodiment is disclosed that addresses the situation where the LV lead is temporarily positioned and an electrode configuration selected and it is desired to test such an arrangement prior to implanting the RV lead. As shown in FIG. 12, a surface ECG is preferably monitored to detect a QRS complex. Upon detection of the QRS complex (e.g., when the ECG signal exceeds the amplitude threshold), a timing window is opened to monitor for activity sensed by the LV lead. Preferably, the LV activity (in one embodiment detected by a peak of the LV activity signal) will occur toward the end of the window, corresponding to a sufficiently large $\Delta$ value; if it occurs too early in the window, the LV lead arrangement (e.g., position and electrode configuration or selected electrodes) will be deemed unsuitable for CRT therapy. An interval 1202 (corresponding to the $\Delta$ value) may be computed between detection of ventricular activity from the ECG signal and corresponding left ventricular activity detected by the IEGM signal. The interval may be compared with a threshold, as described in detail above.

Alternatively, the window may be delayed following the detection of the QRS complex (see the Timing Window (alternate)), for example approximately 30 milliseconds, and if no activity is detected within the window, then the activity either occurs too early or too late and another site is recommended. If activity is detected within the window, then the lead arrangement is deemed suitable.

As shown in FIG. 13, operation begins at step 1302 with the clinician locating the LV lead at a first potential site, selecting a first potential electrode configuration, and attaching the surface ECG electrodes to the patient. At query block 1304, the system monitors the ECG signal for a QRS complex. Upon detection of the QRS complex, operation proceeds to step 1306, and the system opens a window to monitor the LV lead for detection of left ventricular activity. As described above, the window may be opened immediately following the QRS detection, or may be delayed a predetermined period of time.

At query block 1308, if no LV activity is sensed within the window, then operation proceeds to step 1310 and a different placement and/or electrode configuration is recommended for the LV lead. On the other hand, if LV activity is detected within the window, operation proceeds to optional step 1312, where the timing of the LV activity is compared to the QRS detection. As mentioned above, when the opening of the window is delayed following QRS detection, step 1312 is unnecessary. If the window is opened immediately following QRS detection, then step 1312 is preferably included. If the timing of the LV activity relative to the QRS detection (e.g., if the interval between QRS detection and LV activity is sufficiently long) then operation proceeds to step 1314 and the lead arrangement (e.g., position or placement and electrode configuration) is deemed suitable. If not, operation instead proceeds to step 1310 and a different electrode configuration is recommended and optionally a different lead placement.

Once the LV arrangement is selected, operation proceeds to step 1314, and the RV electrode is implanted in the RV. In one embodiment, the RV electrode is placed using the ECG and LV IEGM information as a reference. Alternatively, the RV electrode location can be selected to further increase the separation between detected RV activity and LV activity.

It will be understood by those skilled in the art that the analysis of the electrode configuration and lead placement can be performed by any device that is able to receive electrical signals from the electrodes and process the signals to determine cardiac timing information. For example, the method can be carried out by the implanted pacemaker or defibrillator, which analyzes the information and then may telemeter such information to a programmer or other external device. In addition, the electrodes may be temporarily connected to a pacing system analyzer (PSA), directly to the programmer, or to any other device capable of processing the sensed cardiac activity. For purposes of adjusting or selecting electrode configuration, an implantable device may perform such a process automatically via a program module (e.g., the module 238 of the device 100 of FIG. 2). Such an option may be enabled or disabled as appropriate by a clinician. A programmer or other device optionally interacts with such a program module via telemetry or other control.

It will be understood by those skilled in the art that while the various embodiments are described primarily for patients who suffer from LBBB and who therefore have late-acting left ventricles, the same embodiments can be applied to patients who suffer from RBBB and who therefore have late-acting right ventricles. In those patients, the various embodiments are applied in reverse, i.e., 1) the LV lead is implanted, 2) the RV lead is located at a potential site along with a potential electrode configuration, 3) the $\Delta$ value and/or IVCD value are determined, and 4) the RV lead electrode configuration is adjusted and/or the lead is moved to a new site if the $\Delta$ value and/or IVCD value do not exceed the respective threshold(s).

In yet another embodiment, the system may determine a $\Delta$ value, an IVCD value for right ventricular pacing and left ventricular sensing (IVCD-RV), and an IVCD value for left ventricular pacing and right ventricular sensing (IVCD-LV). Only if each value exceeds a corresponding threshold will the location(s) be deemed suitable; if not, RV and LV arrangements may be altered (e.g., electrode configuration changed and/or lead position changed), and the values recalculated.

The above-described method for improving response to CRT therapy can also be used for other features utilized by implantable cardiac devices. One example of such a feature is biventricular capture verification, and especially beat-to-beat, biventricular capture verification. As will be apparent to those skilled in the art, if the $\Delta$ value is too small, an evoked response sensed in a first chamber may be corrupted by applied stimulation in the second chamber causing fusion, or by far-field sensing in the first chamber of the applied stimulus. Therefore, the methods described herein may be used to determine whether an existing electrode configuration and/or lead placement is suitable for performing biventricular capture verification, or to determine whether electrode configuration and/or lead placement should be altered in order to improve the likelihood of being able to successfully perform capture verification.

Thus, in one embodiment for use in connection with biventricular capture verification, the right-sided arrangement and left-sided arrangement are selected, and the IVCD value is measured. If the IVCD exceeds a preset threshold (e.g., one or more of the thresholds described above), then the left-sided and right-sided arrangements are considered suitable for performing biventricular capture verification. If not, either 1) a clinician is alerted that at least one of the arrangements should be adjusted (e.g., electrode configuration and/or lead position, if possible), 2) the clinician is advised that biventricular capture verification should not be performed given the electrode spacing, or 3) the implanted device may automatically disable the biventricular capture verification feature. Thus, the clinician may alter the left-side arrangement, with the process being repeated until a suitable arrangement is found.

While various exemplary methods refer to interaction with a clinician, an implantable device may be capable of selecting an electrode configuration from a plurality of possible configuration and optionally testing the selected configuration. Such a method may operate in connection with one or more biventricular therapy modules (e.g., consider the aforementioned biventricular capture verification technique, etc.).

FIG. 14 shows a series of tables 1400 that include information regarding electrode configuration and one or more timing parameters. Table 1402 pertains to information acquired at implant or at some initial time. In this example, four possible left ventricular electrode configurations exist. If all of these are tested, then the table 1402 would include the acquired test data (e.g., $\Delta$, IVCD-RL, IVCD-LR, etc.).

At some later point in time (Day N), post-implantation (and post-table 1402), new information is acquired regarding cardiac behavior for at least one of the electrode configurations and included in table 1404. Similarly, table 1406 includes information acquired at day N+M. Accordingly, the information of any two tables may be compared for purposes of diagnosing patient and/or device condition. In particular, a comparison between the electrode configurations may be mapped to the myocardium to understand better behavior of various myocardial regions. In the instance that a selected configuration does not perform adequately (or information indicates that a different configuration may perform or actually performs better than the selected configuration) then the electrode configuration may be adjusted. Such an adjustment may occur automatically via a module of an implanted device or via interaction with an external device.

Figure 15:
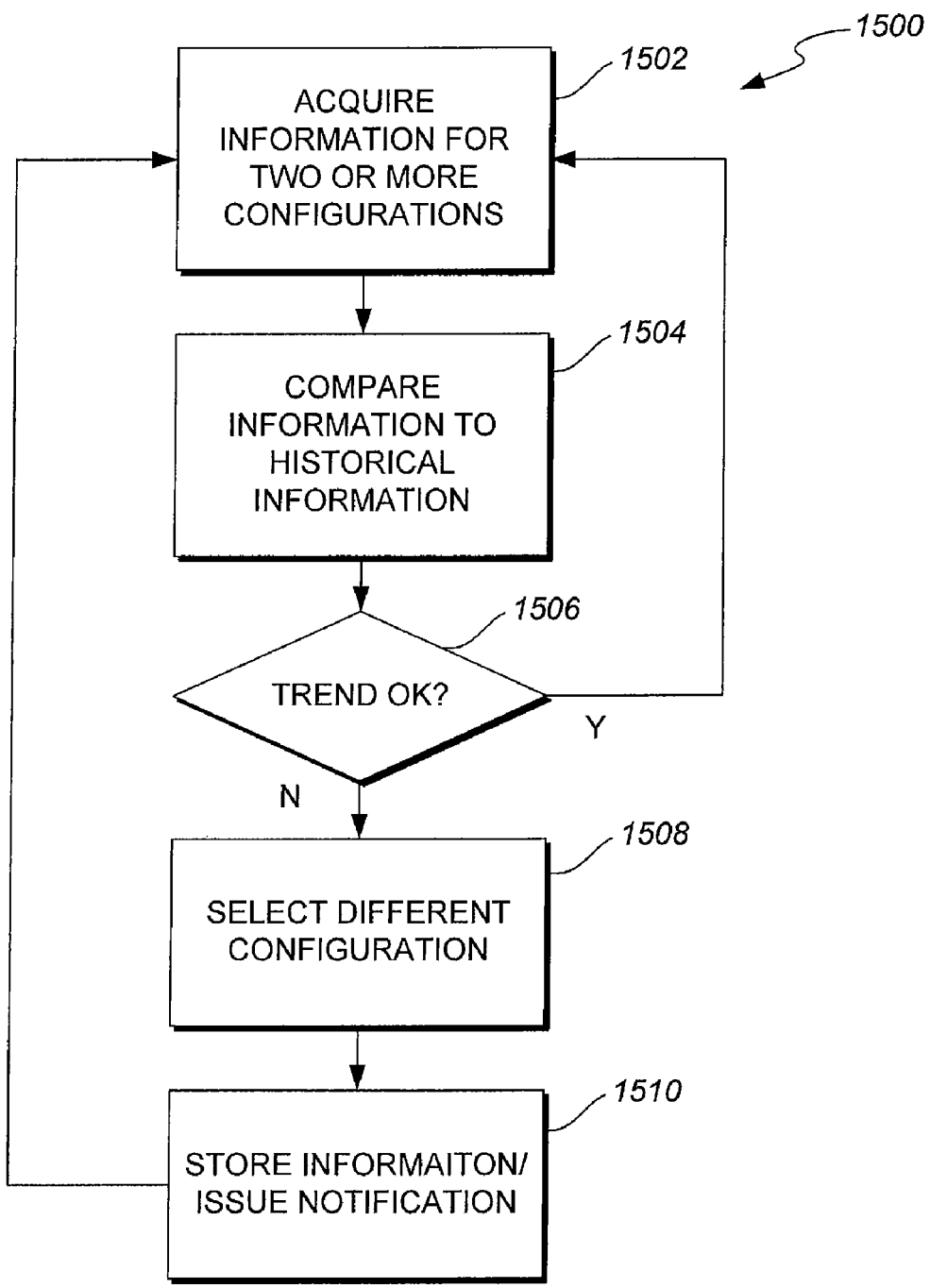
FIG. 15 is a flow chart of an exemplary method that uses information such as the information of the tables of FIG. 14.

FIG. 15 shows a flow chart of an illustrative method 1500. The method 1500 optionally uses information stored in one or more of the tables of FIG. 14 or other information. At step 1502, acquisition of information occurs for two or more selected electrode configurations. For example, IVCD, Δ or other information may be acquired using two or more configurations. At step 1504, a comparison occurs between at least some of the acquired information and historical information. A decision block 1506 decides, based at least in part on the comparison, if a trend exists and, if so, whether the trend is OK (i.e., does not require intervention or a change in arrangement or therapy). In the instance that no trend exists or that the trend does indicate a desire for a change in electrode configuration, the method 1500 continues at the acquisition step 1502 (e.g., optionally after a delay or other action).

In the instance that the decision block 1506 decides that a change in electrode configuration is warranted or that other electrode configurations should be tested, then the method 1500 continues in a selection step 1508 that selects a different electrode configuration. Thereafter, per step 1510, actions may include storage of information, issuance of a notification, etc. If appropriate, the method 1500 continues to the acquisition step 1502.

An exemplary method includes delivering cardiac resynchronization therapy (e.g., bi-ventricular pacing, etc.) to a patient that responds favorable to the therapy, sensing activity of the right ventricle and the left ventricle where the sensing uses an electrode configuration selected from a plurality of electrode configurations associated with electrodes of an implantable lead and optionally a case electrode of an implantable device, determining an interval between sensed activity of the right ventricle and sensed activity of the left ventricle and deciding whether to select a different electrode configuration based at least in part on the interval. A patient that responds favorably may be known as a "responder". Typically a responder shows improved cardiac function after treatment with cardiac resynchronization therapy or other pacing therapy.

Various exemplary methods may occur periodically or according to an event or an instruction. For example, in the aforementioned method, the determining and/or the deciding may occur periodically where, in general, the determining occurs more frequently than the deciding.

Various exemplary methods may occur in vivo using an implantable device and associated equipment (e.g., leads, electrodes, etc.). Various portions of an exemplary method may occur using an external device. For example, in the aforementioned method, the deciding may use information communicated from an implantable device, such as one or more of the intervals, to an external device.

As already mentioned, trends may be established by examining or comparing information over time. For example, an interval trend may be established and used to decide if a change in an electrode configuration is desirable. In the aforementioned method, the deciding may decide to select another electrode configuration if the interval decreases over a period of at least one month.

Various exemplary methods may use a threshold to determine if an interval is appropriate. For example, a threshold for use in determining if an interval is appropriate for cardiac performance (e.g., adequate pacing, etc.) may lie in a range of approximately 30 ms to approximately 150 ms (e.g., an IVCD threshold or a Δ threshold).

Various exemplary methods occur acutely, for example, to monitor cardiac performance, to decide whether equipment is operating properly, to decide whether to change electrode configure, etc.

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   selecting an electrode configuration from a plurality of electrode configurations associated with electrodes of an implantable lead wherein the electrode configuration comprises at least one right ventricular electrode and at least one left ventricular electrode;
   sensing activity of the right ventricle from the right ventricular electrode and the left ventricle from the left ventricular electrode;
   determining an interval between sensed activity of the right ventricle and sensed activity of the left ventricle;
   determining, based at least in part on the interval, whether the selected electrode configuration is suitable for delivery of cardiac resynchronization therapy wherein the determining comprises comparing the interval with a threshold value and determining whether the interval exceeds the threshold value; and
   switching to another electrode configuration only if the selected electrode configuration is not suitable for delivery of cardiac resynchronization therapy, otherwise using the selected electrode configuration for delivery of cardiac resynchronization therapy.

2. The method of claim 1 and further comprising:
   selecting a different electrode configuration if the selected electrode configuration is not suitable.

3. The method of claim 2 and further comprising:
   repeating the sensing and determining after selecting a different electrode configuration.

4. The method of claim 2 wherein:
   the selecting a different electrode configuration comprises selecting at least one electrode associated with the left ventricle.

5. The method of claim 1 wherein:
   the threshold value is between about 30 and about 150 milliseconds.

6. The method of claim 1 and further comprising:
   stimulating the right ventricle if, based on the determining, the selected electrode configuration is not suitable;
   sensing activity of the left ventricle;
   determining a second interval based on the stimulation of the right ventricle and the activity of the left ventricle; and
   deciding, based at least in part on the second interval, whether the selected electrode configuration is suitable.

7. The method of claim 1 wherein:

determining whether the selected electrode configuration is suitable comprises determining whether the selected electrode configuration allows for accurate capture verification.

8. An implantable cardiac therapy system comprising:

at least one lead configured for implant in a patient and comprising a plurality of left ventricular electrodes and at least one right ventricular electrode;

an implantable cardiac therapy device configured to couple to the at least one lead and comprising a controller configured to select an electrode configuration from a plurality of electrode configurations associated with the right ventricular and left ventricular electrodes, to receive sensed activity from the right ventricular and left ventricular electrodes, to determine an interval between sensed activity of the right ventricle and sensed activity of the left ventricle, and to determine, based at least in part on the interval, whether the selected electrode configuration is suitable for delivery of cardiac resynchronization therapy, wherein the determining comprises comparing the interval with a threshold value and determining whether the interval exceeds the threshold value, wherein the controller is operative to switch to another electrode configuration only if the selected electrode configuration is not suitable for delivery of cardiac resynchronization therapy, otherwise to use the selected electrode configuration for delivery of cardiac resynchronization therapy.

9. The implantable cardiac therapy system of claim 8 wherein the controller is configured to select a different electrode configuration if the selected electrode configuration is not suitable.

10. The implantable cardiac therapy system of claim 8 wherein the controller is configured to compare the interval with a threshold value to determine whether the selected electrode configuration is suitable.

11. The implantable cardiac therapy system of claim 8 wherein the controller is configured to determine whether the selected electrode configuration allows for accurate capture verification.

* * * * *